(12) United States Patent
Ryan et al.

(10) Patent No.: US 6,533,811 B1
(45) Date of Patent: Mar. 18, 2003

(54) INTERNAL GRAFT PROSTHESIS AND DELIVERY SYSTEM

(75) Inventors: Timothy J. Ryan, Los Altos Hills, CA (US); Thomas J. Fogarty, Portola Valley, CA (US); Kenneth H. Mollenauer, Santa Clara, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 08/854,089

(22) Filed: May 9, 1997

Related U.S. Application Data

(60) Continuation of application No. 08/714,627, filed on Sep. 16, 1996, now abandoned, which is a continuation of application No. 08/462,218, filed on Jun. 5, 1995, now abandoned, which is a division of application No. 08/089,290, filed on Jul. 8, 1993, now Pat. No. 5,464,449.

(51) Int. Cl.$^7$ .................................................. A61F 2/06
(52) U.S. Cl. .................... 623/1.23; 623/1.11; 623/1.32; 623/1.36; 606/194; 606/195; 606/198
(58) Field of Search ................................ 606/191, 192, 606/194, 195, 198; 623/1.1, 1.11, 1.13, 1.14, 1.23, 1.25, 1.3–1.32, 1.36, 11, 12, 903; 128/898; 604/7–8

(56) References Cited

U.S. PATENT DOCUMENTS

| | | | |
|---|---|---|---|
| 3,509,883 A | 5/1970 | Dibelius | |
| 3,822,238 A | 7/1974 | Blair et al. | 623/66 |
| 3,868,956 A | 3/1975 | Alfidi et al. | |
| 3,993,078 A | 11/1976 | Bergentz et al. | 623/1 |
| 4,130,904 A | 12/1978 | Whalen | 623/1 |
| 4,140,126 A | 2/1979 | Choudhury | |
| 4,300,244 A | 11/1981 | Bokros | 623/1 |

(List continued on next page.)

FOREIGN PATENT DOCUMENTS

| | | | |
|---|---|---|---|
| DE | 1007948 | 5/1957 | |
| DE | 2152142 | 5/1972 | |
| DE | 2528273 | 4/1975 | |
| DE | 5258273 | 10/1976 | |
| EP | 0 461 791 A1 | 12/1991 | A61F/2/06 |
| EP | 0 472 731 A1 | 3/1992 | A61M/29/02 |
| FR | 7537686 | 10/1976 | |
| FR | 7636149 | 11/1976 | |
| FR | 2333487 | 8/1977 | |
| FR | 2391709 | 1/1979 | |
| GB | 1183497 | 3/1970 | |
| GB | 1205743 | 9/1970 | |
| GB | 1565828 | 4/1980 | |
| WO | WO 80/10460 | 7/1980 | |
| WO | WO 80/02461 | 12/1980 | |
| WO | WO 92/19312 | 11/1992 | A61M/31/00 |
| WO | WO 95/09586 | 4/1995 | A61F/2/06 |

OTHER PUBLICATIONS

"A Color Atlas of Ednovascular Surgery" by Rodney A. White and Gilfry H. White, 1990, pp. 84–87.

*Primary Examiner*—David J. Isabella
*Assistant Examiner*—Urmi Chattopadhyay
(74) *Attorney, Agent, or Firm*—Sterne, Kessler, Goldstein & Fox P.L.L.C.

(57) ABSTRACT

A resilient tubular graft is delivered into place within a body passage by elongating the graft to reduce its diameter and then directing the graft to the desired position while in the elongated condition. The graft is carried into position by a pair of elongate members mounted for longitudinal movement relative to one other. Flexible lines secure opposite ends of the graft to the respective elongate members whereby relative longitudinal movement of the members functions to elongate the graft and reduce its diameter. The lines extend around the graft to impart radial compression thereto simultaneously with elongation of the graft. Upon placement of the graft at the desired location within a body passage, the lines are released to permit the graft to expand into engagement with the passage. Barbs on the graft provide for secure engagement of the graft with a body passage.

7 Claims, 7 Drawing Sheets

U.S. PATENT DOCUMENTS

| | | | |
|---|---|---|---|
| 4,441,215 A | 4/1984 | Kaster | 623/1 |
| 4,493,711 A | 1/1985 | Chin et al. | 604/271 |
| 4,572,186 A | 2/1986 | Gould et al. | |
| 4,577,631 A * | 3/1986 | Kreamer | 623/12 |
| 4,650,466 A | 3/1987 | Luther | 604/95 |
| 4,655,771 A | 4/1987 | Walsten | |
| 4,776,337 A | 10/1988 | Palmaz | 623/1 |
| 4,798,193 A | 1/1989 | Giesy et al. | 128/7 |
| 4,872,874 A | 10/1989 | Taheri | 623/1 |
| 4,913,141 A | 4/1990 | Hillstead | 606/194 |
| 4,921,484 A | 5/1990 | Hillstead | 604/104 |
| 5,026,377 A * | 6/1991 | Burton et al. | 606/108 |
| 5,104,399 A | 4/1992 | Lazarus | 623/1 |
| 5,201,757 A * | 4/1993 | Heyn et al. | 623/12 |
| 5,282,824 A | 2/1994 | Gianturro | 623/1 |
| 5,360,443 A * | 11/1994 | Barone et al. | 623/12 |
| 5,456,712 A | 10/1995 | Maginot | 623/1 |
| 5,464,449 A * | 11/1995 | Ryan et al. | 623/12 |
| 5,474,563 A | 12/1995 | Myler et al. | 606/108 |
| 5,507,769 A | 4/1996 | Marin et al. | 606/198 |

* cited by examiner

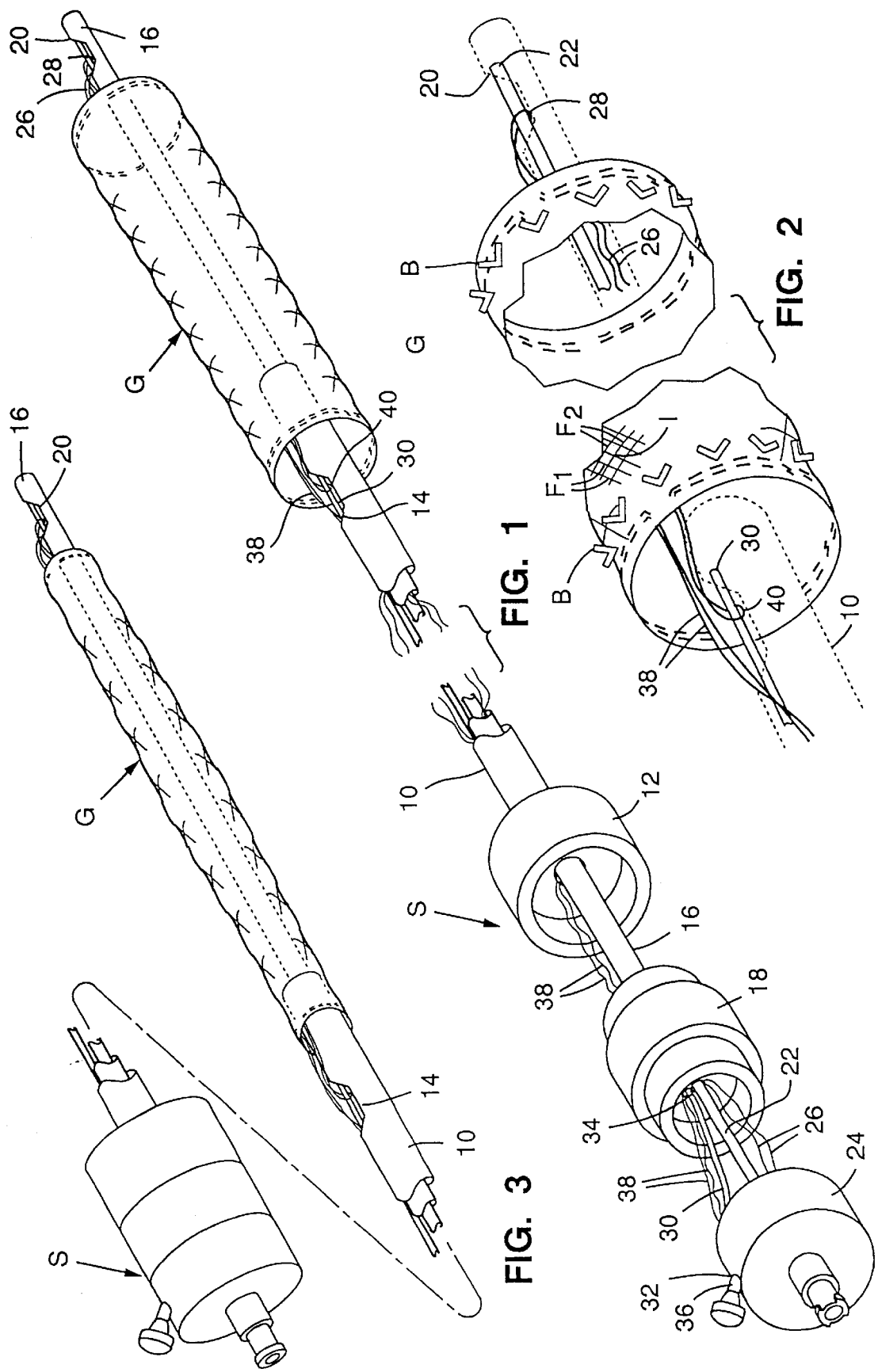

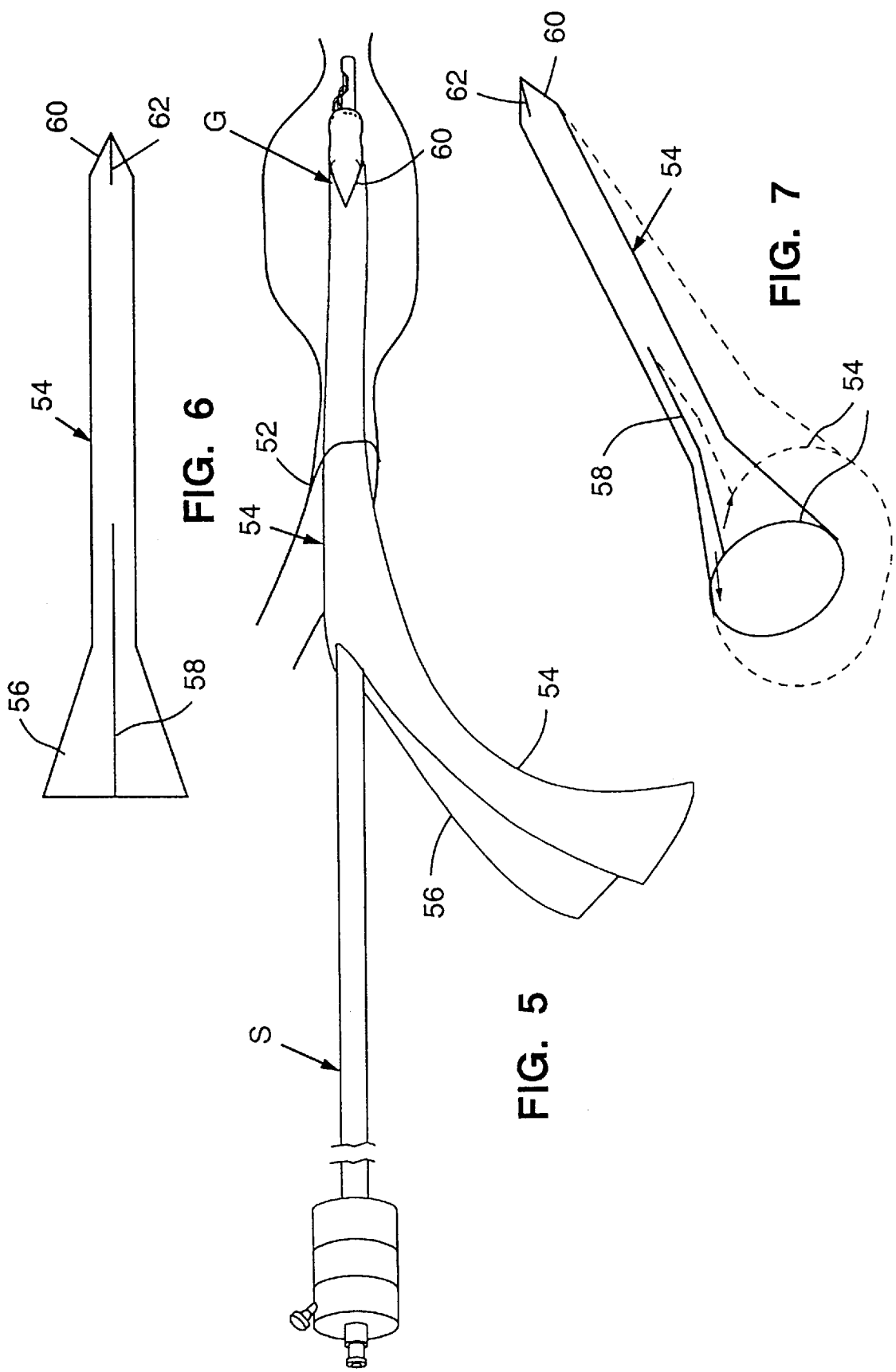

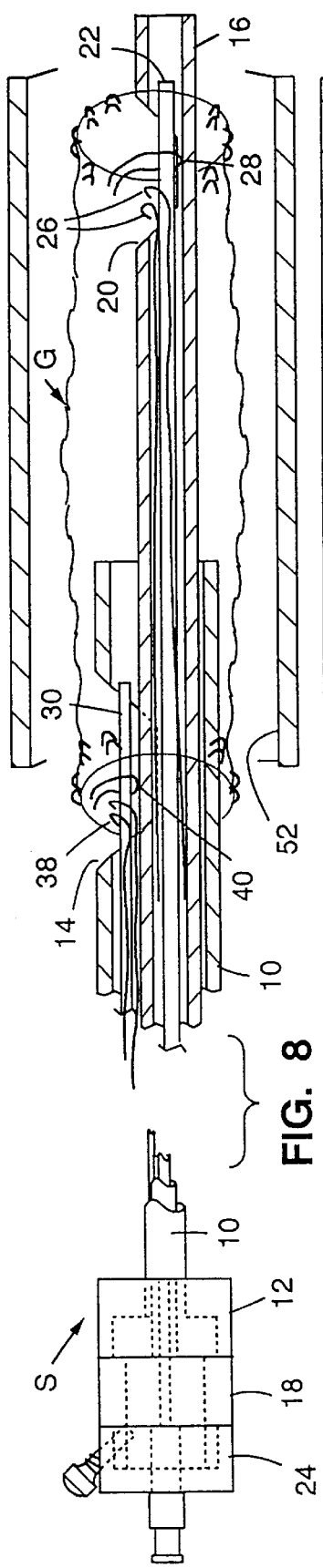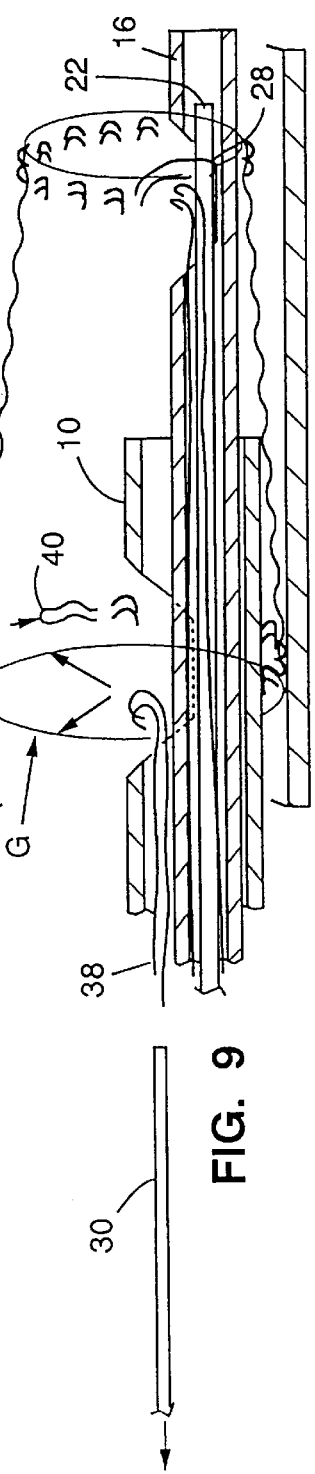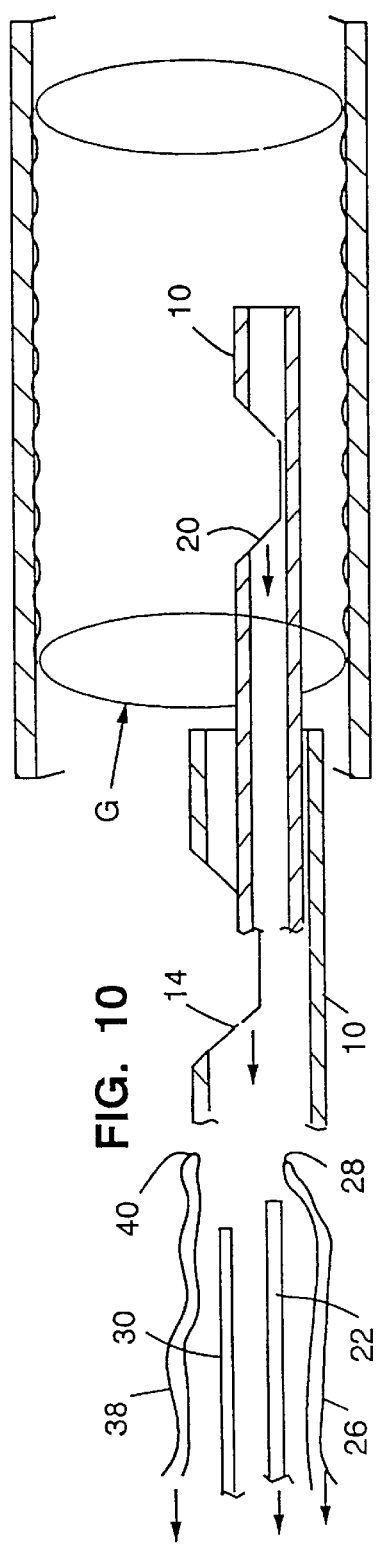

INTERNAL GRAFT PROSTHESIS AND DELIVERY SYSTEM

This is a Continuation of application Ser. No. 08/714,627, filed Sep. 16, 1996, now abandoned, which is a continuation of application Ser. No. 08/462,218, filed Jun. 5, 1995, now abandoned, which is a divisional of application Ser. No. 08/089,290, filed Jul. 8, 1993, now U.S. Pat. No. 5,464,449, the disclosure of which is incorporated by reference.

BACKGROUND OF THE INVENTION

The present invention relates to a prosthetic graft and a method and apparatus for placing the graft within a body passage. In its more particular aspects, the invention is concerned with a resilient tubular graft which may be reduced in diameter for delivery and then expanded into place. The invention is especially concerned with such a graft which may be deployed within the thoracic aorta, the abdominal aorta, or the femoral artery, via a groin incision.

The prior art teaches expansible tubular grafts for use in body passages. For example, U.S. Pat. No. 4,655,771 discloses such a graft which may be elongated for delivery and then expanded into place. With the device of that patent, the ends of the graft are held within tubular fixtures which are used to impart elongation to the graft to reduce its diameter during delivery. Once the graft is in place, these fixtures are removed to release the graft for expansion. The employment of the fixtures necessarily adds to the-bulk and complexity of the mechanism and limits its use.

Another example of an expansible intraluminal graft is found in U.S. Pat. No. 4,776,337. The device of that patent is fabricated of a malleable material which is delivered in a reduced diameter condition and, once in place, expanded by an angioplasty balloon to dilate and expand the lumen of a blood vessel.

The prior art also teaches expansible devices for vessel dilation embodying braided cylinders of an adjustable axial length structured such that a reduction in the length increases the radial size of the device. U.S. Pat. No. 4,572,186 shows such a device.

It is also known to provide sheaths which may be placed in vessels to facilitate the passage of other instruments or catheters therethrough. U.S. Pat. Nos. 4,493,711 and 4,798,193 teach such devices.

SUMMARY OF THE INVENTION

The graft of the present invention is resilient and of a tubular configuration adapted to assume a foreshortened enlarged diameter condition upon relaxation and, upon being elongated, assume a reduced diameter condition. The mechanism for delivery of the graft comprises an elongate placement means which extends longitudinally of the graft to carry the graft through a body passage and facilitate its placement. Flexible lines secure opposite ends of the graft to the elongate placement means. The lines are movable to selectively elongate the graft for delivery, or expand the graft for placement. A retractable sheath may be provided to shield the mechanism and graft during the delivery process.

The method of the invention comprises the steps of securing opposite ends of the graft to a placement member with flexible lines, moving the lines to elongate the graft, passing the placement member through a body passage with the graft carried thereby in a reduced diameter elongated condition, and positioning the graft and releasing the lines at the desired location. In the preferred embodiment the lines are also extended around the graft to subject it to radial compression simultaneously with its elongation.

A principal object of the invention is to provide an improved graft and system and method for its delivery and placement which enables the graft to be delivered through elongate body passages.

Another object of the invention is to provide an improved expansible tubular graft which may be fabricated with fluid permeable, or impermeable, walls.

Still another object is to provide such a graft which is biocompatible with the body and has means to securely anchor it in place.

A further object is to provide such a graft which may be securely placed with a main artery without blocking branch arteries, even where there is not a substantial length of healthy artery between the aneurysm being treated and the branch arteries.

Yet another more general object of the invention is to provide an improved apparatus and method for intraluminal delivery of a graft to a select remote area within a body passage, without need to surgically access the area.

Yet a further object of the invention is to provide an apparatus and method for the intraluminal placement of a graft within a body passage which may be carefully controlled to provide precise placement of the graft and repeatedly adjusted.

Still another object related to the latter object is to provide such an apparatus and method wherein the graft can be precisely located and fully expanded before its release from the delivery system.

These and other objects will become more apparent from the following detailed description and accompanying drawings.

BRIEF DESCRIPTION OF THE DRAWINGS

FIG. 1 is an exploded perspective view of the graft and delivery system.

FIG. 2 is an enlarged perspective view of the graft end of the delivery system shown in FIG. 1, with the graft in radially expanded condition.

FIG. 3 is an enlarged perspective view similar to FIG. 2, with the graft shown in a radially contracted condition.

FIG. 5 is a side view of the delivery system and the sheath which may be used to introduce the system into an artery.

FIG. 6 is a side view of the sheath shown in FIG. 5, without the delivery system.

FIG. 7 is a perspective view of the sheath of FIGS. 5 and 6.

FIG. 8 is cross-sectional side view of the delivery system within an artery, with the graft shown in radially contracted condition.

FIG. 9 is a cross-sectional side view, with parts thereof broken away, showing the delivery system mechanism in the process of releasing the graft.

FIG. 10 is a cross-sectional side view showing the delivery system as it has fully released the graft within a body passage, at the commencement of removal of the system from the passage.

DESCRIPTION OF THE PREFERRED EMBODIMENT

FIG. 1 shows the graft and delivery system in exploded perspective, with the graft designated by the letter G and the delivery system designated in its entirety by letter S. The graft, as may be seen in FIG. 2, is of an open-ended tubular configuration and comprises filaments $F_1$ and $F_2$ extending helically therearound. The filaments $F_1$ and $F_2$ extend around the graft in opposite directions and cross at intersections I. The filaments are fabricated of a resilient material, such as polyester, titanium or stainless steel. The filaments cross over each other at intersections I. As a result of the resiliency of the filaments, the graft normally assumes a foreshortened enlarged diameter upon relaxation and, upon being elongated, assumes a reduced diameter condition (see FIG. 3). In a typical embodiment for use in treating a dissecting aneurysm in the aorta, the graft might have the following dimensions:

| ELEMENT | DIMENSION |
| --- | --- |
| Filament diameter | .010 inches |
| Graft diameter in the relaxed condition | 1.0–1.25 inches |
| Graft length in the relaxed condition | 3.0–6.0 inches |

In a typical application, the graft is elongated to double its length for delivery, with the result that the outside diameter of the graft is reduced by substantially more than one-half.

Figure 4:
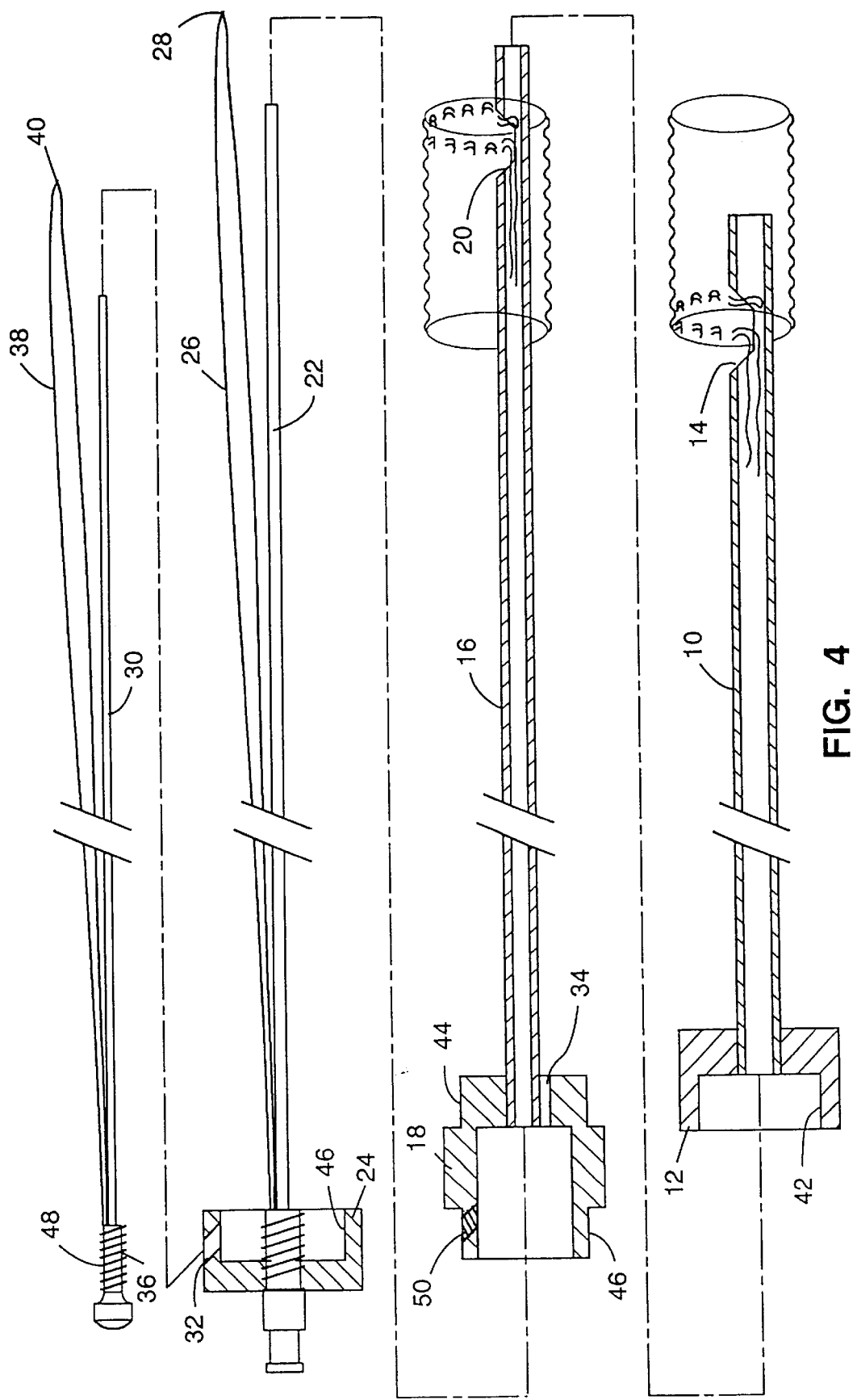
FIG. 4 is an exploded side view of the delivery system, with parts shown in cross-section.

The components of the delivery system may best be seen from FIG. 4 and comprise:

1. An outer tube 10 having an outer hub 12 fixed to its proximal end and a lateral opening 14 adjacent its distal end;
2. A middle tube 16 proportioned for slidable extension through the outer tube 10, said middle tube having a middle hub 18 fixed to its proximal end and a lateral opening 20 adjacent its distal end;
3. A flexible distal retainer rod 22 proportioned for slidable extension through the middle tube 16, said rod having a rod hub 24 fixed to its proximal end;
4. A closed loop flexible line 26 fixed at one end to the hub 24 and closed at its distal end 28;
5. A proximal suture loop retainer wire 30 proportioned for slidable extension through an opening 32 formed in one side of the hub 24 and through a passage 34 formed in the middle hub 18, said retainer wire having a retainer hub 36 fixed to its proximal end; and,
6. A looped flexible line 38 fixed at its proximal end to the hub 36 and closed at its distal end 40.

FIG. 1 shows the delivery system in the assembled condition, with the outer hub, middle hub and rod hub exploded relative to one another for purposes of illustration. The middle tube 16 extends slidably through the outer tube 10. The retainer rod 22, together with the looped flexible line 26 extends through the middle tube 16 and the closed distal end 28 of the line 26 extends through the opening 20 and around the graft G. The wire 30, together with the looped flexible line 38, extends through the opening 32 in the hub 24 and thence through the opening 34 in the hub 18 and through the hub 12 and the outer tube 10. From the latter, it will be appreciated that there is sufficient space between the outer tube 10 and the middle tube 16 to accommodate free passage of the wire 30 and looped line 38 therethrough. The looped flexible line 38 exits the tube 10 through the opening 14 and extends around the graft G.

FIG. 2 shows in detail the manner in which the looped lines 26 and 38 extend around the graft G. As there shown, it will be seen that the looped line 38 is threaded into and out of the graft around its proximal end and exits from the graft to a closed end 40 engaged around the retainer wire 30. The looped flexible line 26 is fed into and out of the graft G around its distal end and exits therefrom, with the end 28 engaged around the rod 22. Thus, with the rod 22 and wire 30 in place as shown in FIG. 2, the looped ends of the lines 26 and 38 are secured around the distal and proximal ends, respectively, of the graft G. In this condition, movement of the hub 12 into mated engagement with the middle hub 18 functions to elongate the graft G and cinch the ends of the looped lines around the graft, as shown in FIG. 3. Such elongation and cinching reduces the diameter of the graft by substantially more than one-half.

From FIG. 4 it will be seen that the hubs are configured to mate one within the other in a nested condition. Hub 12 has a recess 42 proportioned to receive a collar 44 formed on one end of the hub 18. A collar 46 formed on the other end of the hub 18 is proportioned for mating engagement within a recess 46 formed in the hub 24. The retainer hub 36 is formed with screw threads 48 formed for threaded engagement with a threaded opening 50 in the hub 18. When the hubs are fully nested, the opening 32 is aligned with the opening 50 and the hub 36 is passed through the opening 32 into threaded engagement with the opening 50.

FIG. 5 shows the delivery system fully assembled, with the hubs nested together and the graft G in the fully elongated reduced diameter condition. As there shown, the graft is in the process of being introduced into the femoral artery 52 through a partially split sheath 54. The sheath has a length equal to or slightly greater than that of the delivery system and, during the delivery process, fully encloses that part of the system disposed within the artery. Once fully in place at the site where it is desired to locate the graft, the sheath is partially withdrawn, as shown in FIG. 5, to expose the graft.

FIGS. 6 and 7 show the detailed construction of the sheath. The sheath is preferably made of a flexible material having a relatively low coefficient of friction, such as polyethylene or TEFLON. The proximal end of the sheath, designated 56, is of an open funnel-shaped configuration with a slit 58 extending over its length. The distal end of the sheath, designated 60, is of a closed conical configuration with a slit 62 extending thereacross to permit the delivery system to be passed therethrough, as shown in FIG. 5.

The graft G may be either fluid permeable or impermeable, or a combination of permeable and impermeable portions, depending upon the area of its intended use. Permeability naturally results from the spacing of the filaments $F_2$. Impermeability may be provided by coating the graft with an elastomer, such as silicone.

Operation

The operation of the graft and delivery system may be seen from FIGS. 8, 9 and 10. In FIG. 8, the graft is shown in the elongated contracted condition, with the sheath retracted prior to expansion and release of the graft from the delivery system. Expansion is provided by moving the hub 12 forwardly away from the hub 18 which, in turn, moves the distal end of the outer tube 10 toward the distal end of the middle tube 16 (See FIG. 9) and permits the graft to foreshorten and expand into engagement with the artery. If the graft is not positioned at the precise location desired, it may be re-elongated by moving the hub 12 into engagement with the hub 18 and repositioned. Once the graft is expanded at the precise location desired, it is released from the delivery system by first withdrawing the wire 30 and the flexible line 38 and then withdrawing the rod 22 and the flexible line 26. Withdrawal of the wire 30 and the rod 22 releases the looped distal ends 40 and 28 of the lines. Once the lines are so released, proximal pulling of the lines (See FIG. 10) pulls the lines from the graft and out of the delivery system. The remaining components of the system can then be fully withdrawn from the artery through the groin incision. The sheath 54 may be left in place to facilitate such withdrawal.

The graft may also be provided with barbs B for engagement with the body passage within which the graft is used. Such barbs, as shown in FIG. 2, may comprise folded-over titanium staples passed through the material of the graft.

Figure 11:
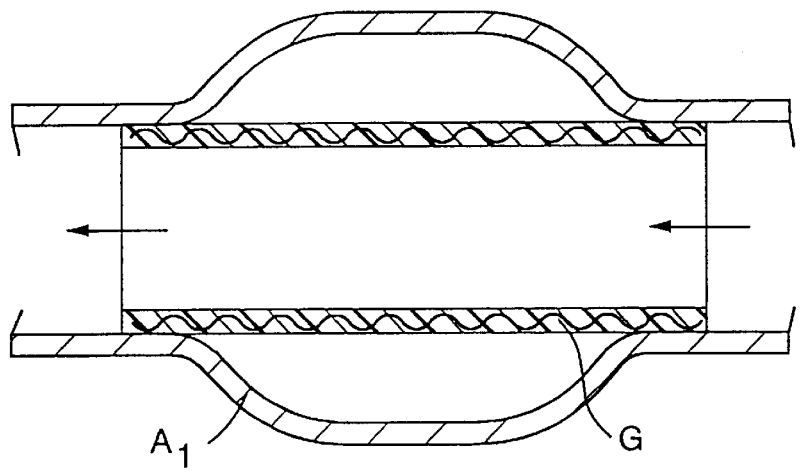
FIG. 11 is a cross-sectional side view showing an artery with an aneurysm and a graft with impermeable side walls which has been placed within the aneurysm according the present invention.
Figure 12:
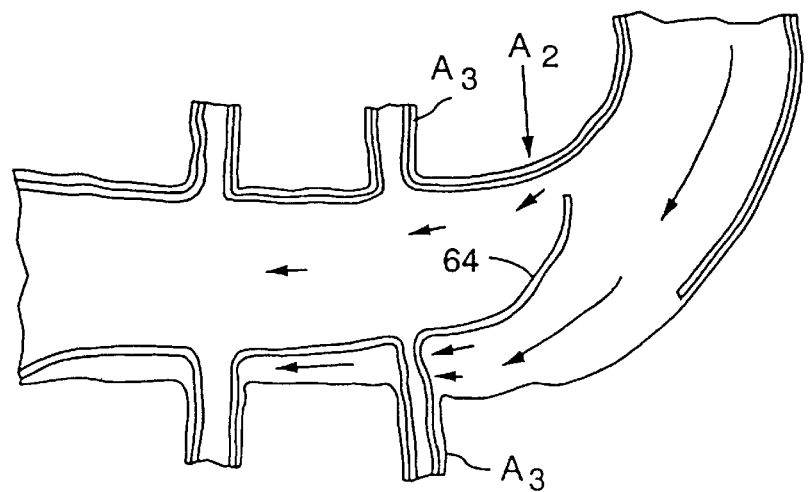
FIG. 12 is a cross-sectional side view showing an artery having a dissecting aneurysm; prior to treatment of the aneurysm through means of the graft of the present invention.
Figure 13:
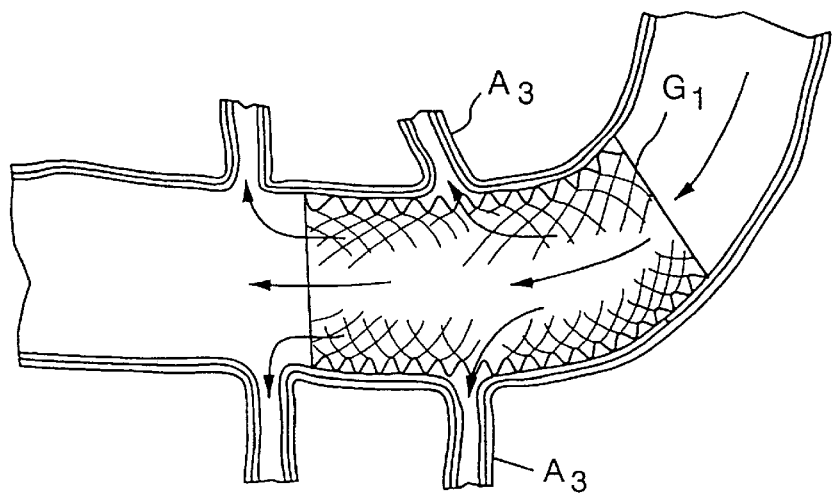
FIG. 13 is a cross-sectional side view of an artery corresponding to that of FIG. 12, diagrammatically showing how the lumen of the artery is forced open through a graft placed with the present invention.
Figure 14:
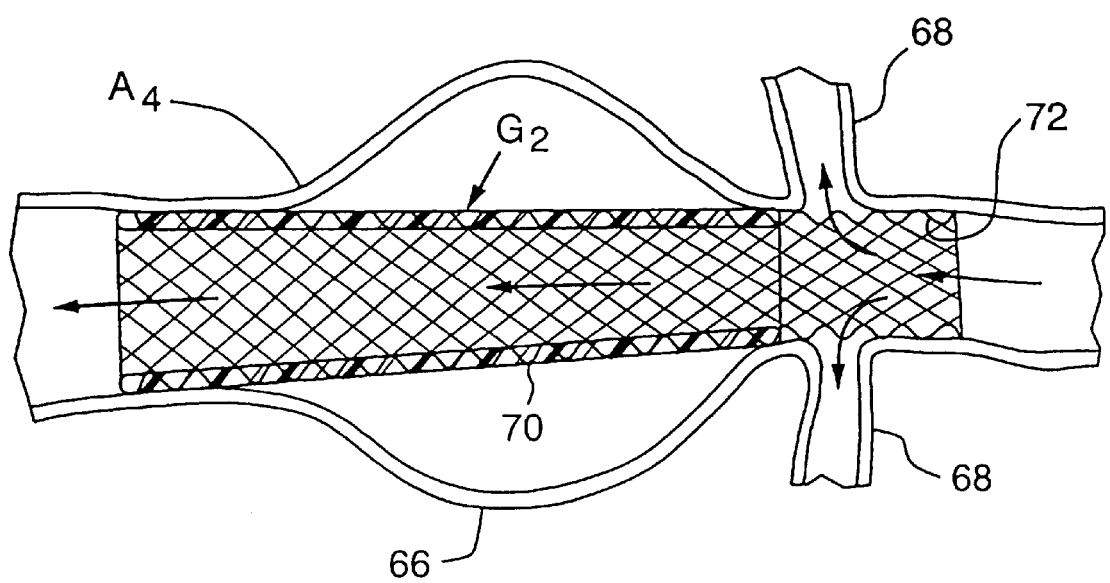
FIG. 14 is a cross-sectional side elevational view of an artery which does not have a substantial length of healthy artery between itself and the renal arteries; showing a graft placed according to the present invention to treat any aneurysm within the artery while permitting flow to the renal arteries.

FIGS. 11, 12, 13 and 14 show different applications of the graft. In FIG. 11, an impermeable coated form of the graft G is shown within an artery $A_1$ at the site of an aneurysm which is shielded by the graft. The coating on the graft is designated by the letter C. FIG. 12 shows an artery $A_2$ having a dissecting aneurysm 64. FIG. 13 shows the same artery $A_2$ with its lumen forced open by a permeable form of the graft, designated $G_1$. In this application, the permeable character of the graft permits blood to flow from the artery $A_2$ into the branches $A_3$. The arrow lines in FIGS. 12 and 13 depict the direction of the flow of blood. As shown in FIG. 13, the graft G, compresses the aneurysm and permits free flow through the artery. FIG. 14 shows an artery $A_4$ having an aneurysm 66 without a substantial length of healthy artery between the aneurysm and renal arteries 68. As there shown, a graft $G_2$ having an impermeable portion 70 and a permeable portion 72 is used. The impermeable portion 70 is positioned over the aneurysm 66 and adjacent healthy tissue and the permeable portion 72 is placed over the renal arteries 68 and adjacent healthy tissue of the artery $A_4$. Thus, the graft bridges the aneurysm and the renal arteries, allowing flow through all arteries and providing for positive graft fixation.

Figure 15:
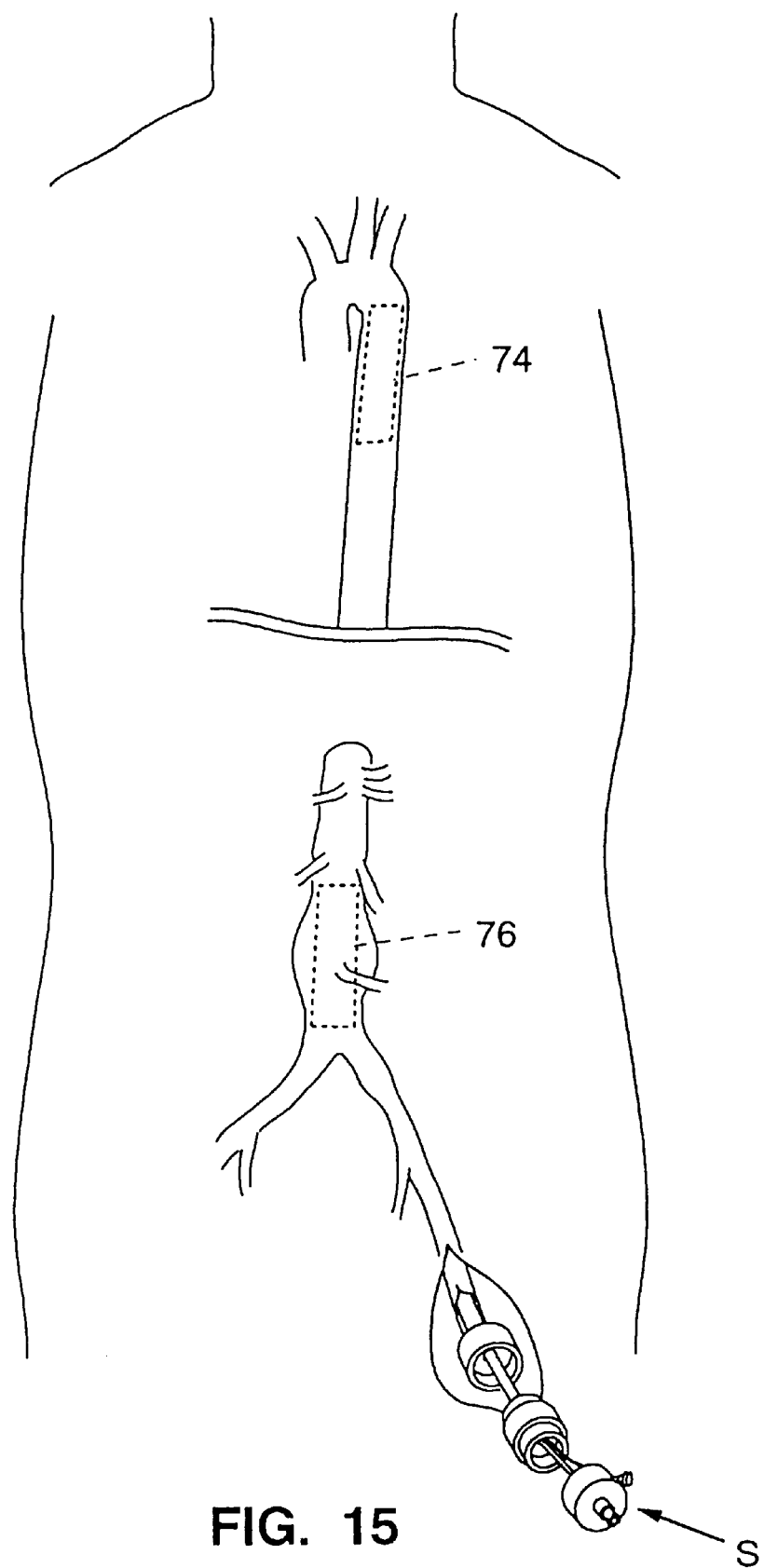
FIG. 15 is a cross-sectional view of the body, showing the thoracic and abdominal aorta and the manner in which the system of the present invention can be used to deliver grafts to select areas of the aorta.

FIG. 15 shows the manner in which the graft may be inserted into the femoral artery through a groin incision and directed to treat a dissecting thoracic aneurysm, such as that shown in FIGS. 12 and 13, or an abdominal aortic aneurysm. Dashed lines 74 depict where the graft would be positioned for treating a dissecting thoracic aneurysm. Dashed lines 76 depict where the graft would be positioned for treating an abdominal aortic aneurysm. Because of the side branches at the thoracic aneurysm, the permeable embodiment of FIG. 13 would be used at that location. The abdominal aortic aneurysm would be treated with the impermeable graft embodiment of FIG. 11.

CONCLUSION

From the foregoing description, it is believed apparent that the present invention enables the attainment of the objects initially set forth herein. In particular, a graft and delivery system is provided which may be delivered to remote locations to treat various types of aneurysms. It should be understood, however, that the invention is not intended to be limited to the illustrated embodiment, but rather is defined by the accompanying claims.

What is claimed is:

1. A tubular graft for treating aneurysm within a major artery wherein branch arteries extend from the major artery in close proximity of the aneurysm and a system for placing the graft within an artery, said graft being fabricated of a resilient material and adapted to reduce in diameter upon elongation, said graft and system comprising:

a first elongate substantially fluid impermeable portion adapted to be positioned over the aneurysm so as to shield the aneurysm from blood flow through the major artery;

a second elongate substantially fluid permeable portion contiguous with the first portion, said second portion being adapted to extend over the branch arteries when the first portion is positioned over the aneurysm, said second portion engageable against the major artery surrounding the branch arteries to affix the position of the graft when deployed;

first and second elongate members extending longitudinally of the graft means, said members being longitudinally movable relative to one another and the graft means;

securing means releasably attaching the elongate members to the tubular graft means whereby longitudinal movement of the elongate members relative to one another in one direction elongates the graft means and longitudinal movement of the members in an opposite direction relaxes the graft means for expansion to the foreshortened enlarged diameter condition; and, means to selectively release the securing means from the elongate members.

2. A tubular graft for treating aneurysm within a major artery wherein branch arteries extend from the major artery in close proximity of the aneurysm and a system for placing the graft within an artery, said graft being fabricated of a resilient material and adapted to reduce in diameter upon elongation, said graft and system comprising:

a first elongate substantially fluid impermeable portion adapted to be positioned over the aneurysm so as to shield the aneurysm from blood flow through the major artery;

a second elongate substantially fluid permeable portion contiguous with the first portion, said second portion being adapted to extend over the branch arteries when the first portion is positioned over the aneurysm, said second portion engageable against the major artery surrounding the branch arteries to affix the position of the graft when deployed;

elongate placement means extending longitudinally of the graft to carry the graft through the body passage;

flexible lines securing opposite ends of the tubular graft means to the placement means;

means to move said lines to selectively elongate the graft means; and, means to selectively release the flexible lines from the placement means.

3. A method of treating an aneurysm within a major artery wherein branch arteries extend from the major artery in close promimity of the aneurysm, said method comprising:

providing a tubular craft of an outside diameter closely approximating the internal diameter of the major artery and a length exceeding that of the aneurysm, said graft being fabricated of a resilient material and adapted to reduce in diameter upon elongation and having:

a first elongate substantially fluid impermeable portion; and, a second elongate substantially fluid permeable portion contiguous with the first portion;

elongating the graft to reduce its outside diameter to less than the internal diameter of the major artery;

passing the graft into the major artery and over the aneurysm;

positioning the graft and relaxing its elongation to expand the first portion into a condition covering the aneurysm and the second portion into a condition covering at least some of the branch arteries;

affixing the graft within the major artery by engaging the major artery with the second portion adjacent the at least some of the branch arteries;

extending first and second elongate members along the graft for longitudinal movement relative to one another and the graft;

securing a first end of the graft to an attachment point on said first elongate member and a second end of the graft to an attachment point on said second elongate member; and moving said members longitudinally relative to one another to move the attachment points apart and, thereby, elongate the graft;

moving said elongate members longitudinally relative to one another to move the attachment points together and, thereby, relax elongation of the graft and permit the graft to expand resiliently into engagement with the passage; and disconnecting the graft from the elongate members and removing the members from the passage.

4. A method for treating an aneurysm within a major artery, wherein a branch artery extends from the major artery at a branch intersection, the intersection in close proximity of the aneurysm, the method comprising:

introducing a tubular vascular graft into the major artery while the graft is in a small diameter configuration, the graft comprising a plurality of filaments which define a perforates tubular frame, the filaments extending along a substantially fluid impermeable axial portion of the graft and along a fluid permeable axial portion of the graft;

positioning the fluid impermeable portion of the graft within the major artery in axial alignment with the aneurysm and with the fluid permeable portion in axial alignment with the intersection; and radially expanding the frame so that the filaments along the fluid permeable portion radially engage the major artery surrounding the branch artery to anchor the graft within the major artery, the fluid permeable portion of the graft covering the branch artery such that bloodflow between the major artery and the branch artery passes through the expanded fluid permeable portion, the expanded fluid impermeable portion isolating the aneurysm from bloodflow through the major artery.

5. A method as claimed in claim 4, wherein the major artery comprises the aortic artery, and wherein the fluid permeable portion covers the renal arteries.

6. A method as claimed in claim 4, wherein the filaments comprise resilient structures which resiliently engage the surrounding major artery.

7. A method as claimed in claim 6, wherein the filaments comprise a resilient material and extend helically around the graft in opposite directions so that the frame expands axially when resiliently compressed radially, and wherein an elastomeric material is supported by the filaments along the fluid impermeable portion of the graft to isolate the aneurysm from the bloodflow.

* * * * *

UNITED STATES PATENT AND TRADEMARK OFFICE
CERTIFICATE OF CORRECTION

PATENT NO.   : 6,533,811 B1
DATED        : March 18, 2003
INVENTOR(S)  : Ryan et al.

It is certified that error appears in the above-identified patent and that said Letters Patent is hereby corrected as shown below:

<u>Title page,</u>
Item [56], References Cited, FOREIGN PATENT DOCUMENTS,
-- FR 1 602 513 1/1971 -- should be added.

<u>Column 7,</u>
Line 10, "craft" should be -- graft --.

Signed and Sealed this

Twenty-eighth Day of October, 2003

JAMES E. ROGAN
*Director of the United States Patent and Trademark Office*